United States Patent [19]

Pace et al.

[11] 4,265,673

[45] May 5, 1981

[54] POLYMER SOLUTIONS FOR USE IN OIL RECOVERY CONTAINING A COMPLEXING AGENT FOR MULTIVALENTIONS

[75] Inventors: Gary W. Pace; Trevor J. Holding, both of Knowsley, England

[73] Assignee: Talres Development (N.A.) N.V., Curacao, Netherlands Antilles

[21] Appl. No.: 50,322

[22] Filed: Jun. 20, 1979

[30] Foreign Application Priority Data

Jun. 23, 1978 [GB] United Kingdom ............... 27803/78

[51] Int. Cl.$^3$ ............................................. C08L 33/26
[52] U.S. Cl. ..................... 106/177; 106/181; 106/194; 106/203; 106/205; 106/208; 252/8.55 D; 260/29.6 H; 260/29.6 MP; 260/29.6 MN
[58] Field of Search ............... 106/177, 181, 194, 203, 106/208, 205; 252/8.55 D; 260/29.6 H, 29.6 MP, 29.6 MN

[56] References Cited

U.S. PATENT DOCUMENTS

| | | | |
|---|---|---|---|
| 3,532,166 | 10/1970 | Williams | 166/274 |
| 3,853,771 | 12/1974 | Felmann et al. | 252/8.55 B |
| 4,049,054 | 9/1977 | Wier | 166/273 |
| 4,078,607 | 3/1978 | Carter et al. | 166/246 |
| 4,119,546 | 10/1978 | Wernau | 166/305 R |
| 4,128,482 | 12/1978 | Knight | 252/8.55 D |

FOREIGN PATENT DOCUMENTS

2734364 2/1978 Fed. Rep. of Germany .

*Primary Examiner*—Maurice J. Welsh
*Attorney, Agent, or Firm*—Ostrolenk, Faber, Gerb & Soffen

[57] ABSTRACT

A process for preparing a polymer solution for use in "polymer based" oil recovery comprises adding to water the polymer in the form of an aqueous solution, a dry particulate solid or a suspension in a non-aqueous liquid, and also adding a complexing agent for multivalent ions and, where the solution so formed does not already contain an alkali metal salt, subsequently incorporating therein an alkali metal salt. The polymer may be a substantially cell-free microbial polysaccharide gum, a polyacrylamide or a cellulose derivative.

18 Claims, No Drawings

POLYMER SOLUTIONS FOR USE IN OIL RECOVERY CONTAINING A COMPLEXING AGENT FOR MULTIVALENTIONS

The present invention relates to a process for preparing a solution of a polymer for use in oil recovery, and more particularly to the use of complexing agents in such processes.

Typically, oil is recovered from underground reservoir deposits by a series of operating procedures. A new borehole generally gives a limited quantity of oil as a result of the liberation of internal pressure in the borehole. When this pressure is over, it becomes necessary to pump out further amounts of the oil from the oil-bearing formation with the help of mechanical devices. However, these procedures recover only about 25% of the total oil present in the deposit, and a large portion of the oil remains trapped within the pores of the formation.

A further increase in oil recovery can be achieved by means of the so-called "secondary recovery". In one method, water is pumped down a borehole or a number of boreholes and a part of the trapped oil is displaced from the porous stone or other kind of formation, and the displaced oil is collected through the surrounding boreholes. However, water displacement still leaves about 55 to 60% of the available oil trapped in the formation, primarily because water possesses a very low viscosity in relation to crude oil and displays the tendency to follow the path of least resistance so that it finds its way through the rock and leaves large pockets of oil untouched. A number of methods have been developed in recent years for the recovery of further quantities of oil from these deposits by the use of so-called "mobility regulating solutions". Such solutions increase the displacement of the oil by decreasing the mobility of the displacing fluid so that it can permeate the rock more throughly. Of interest are those recovery processes which use polymer displacement with a polysaccharide, such as xanthan gum, or polyacrylamide serving to increase the viscosity of the displacing fluid.

The present invention is concerned with the use of viscous polymer solutions to enhance oil recovery from oil-bearing formations. More specifically, the invention is concerned with improving the injectability of such solutions, as will be considered below.

Before so doing, it is first necessary to point out that the invention relates to "simple" polymer solutions, "simple" being used in the sense that we are not concerned with the use of polymer solutions containing surfactants. It is known to recover oil using water to which a surfactant has been added to lower surface tension between the injected solution and the oil to be recovered. In a variation, a polymer such as a polyacrylamide, cellulose ether or polysaccharide is incorporated in the surfactant solution. This variation is the subject, for example, of U.S. Pat. No. 4049054 and as mentioned in the specification of that U.S. Patent, it is possible further to add additives such as builders. Typical builders include sodium tripolyphosphate, a chelating agent, to cooperate with the surfactant to increase its detergent power.

When injecting polymer solutions, particularly xanthan gum solutions, one drawback which is often encountered is a tendency for the solutions to block the oil-bearing formations into which they are injected. It is generally held that this blocking tendency may arise from several causes which include the presence of residual solids in the solution and a propensity to precipitate or form gels when injected into alkaline formations.

Typical residual solids which may be present in xanthan gum or other heteropolysaccharide solutions include whole bacterial cells or cell debris arising from the fermentation process conventionally used for producing the heteropolysaccharide. W. German Offenlegungsschrift No. 2734364 discusses this aspect of the use of xanthan gum and discloses a fermentation method by which a gum practically free from insoluble material of greater than 3 microns can be obtained.

In particular, the Offenlegungsschrift lists five main factors which make this result possible. The factors all relate to careful control of the fermentation conditions, and as the third such factor, it is specified that hard water with high concentrations of calcium ions is not used in the preparation of the fermentation medium. To this end, a chelating agent such as ethylenediamine tetraacetic acid or preferably citric acid is added to sequester excess calcium and prevent precipitation of calcium ions as an insoluble phosphate. When taken with the other measures outlined in the specification, it is then said to be possible to obtain a product with substantially no insoluble material of size above about 3 microns. In summary, the chelating agent is thus added before or during fermentation. In its analysis of pertinent prior art, the Offenlegungsschrift 2,734,364 mentions that U.S. Pat. No. 3,853,771 solves the blocking problem of whole fermentation broths by a process for dissolving or dispersing cellular microorganisms which comprises bringing this material (i.e. whole fermentation broth) into contact with an aqueous dispersing solution containing a surface active agent, a chelating agent, and an alkali metal hydroxide. The surface active agent acts to disperse the outer walls of the microorganism cells and the chelating agent acts to disperse the inner walls thereof, while the hydroxide encourages these dispersing effects. The U.S. Patent is thus considered to disclose a variation in which chelating agent along with other components is added after fermentation to the broth containing the desired polysaccharide along with residual solids such as cellular microorganisms.

Reference to the U.S. Patent itself, however, shows that it is not concerned with the blocking problem of whole fermentation broths resulting from production of heteropolysaccharide gums. Instead it is concerned with dispersing bacteria such as *Desulfovibrio desulfuricans* which naturally grow in oil-containing formations. The dispersing solution is injected at the well-head as part of an oil recovery process based on the injection of water. Insofar as one is concerned with the use of complexing agents in the preparation of solutions of polymers for use in oil recovery, the actual U.S. Pat. No. 3853771 is of less relevance than the discussion thereof to be found in W. German Offenlegungsschrift No. 2734364.

Regarding the propensity for xanthan gums to precipitate or form gels, the currently accepted theory is that aggregation is primarily brought about by di- or trivalent ions present in the solution, the aggregate polymer then forming a precipitate or a gel. D. Lipton in his paper SPE 5099 prepared for the 49th Annual Fall Meeting of the Society of Petroleum Engineers of AIME, Oct. 6-9, 1974, discusses this phenomenon and others which affect injectability of biopolymers, and mentions that gel formation is generally encountered at above pH 9. Gelation or precipitation under alkaline conditions in the presence of multivalent ions has also been put forward by H. J. Hill et al (SPE 4748, Improved Oil Recovery Symposium, Tulsa 1974) to explain a failure to obtain reproducable experimental results with xanthan gum solutions, but no evidence was found for gel formation with polyacrylamide solutions such as are used for oil recovery.

We have now found that the injectability of a solution of a polymer at acid or approximately neutral pH can be improved by the inclusion of a complexing agent for complexing multivalent ions. This finding applies generally to the viscous polymer solutions employed for "polymer-based" oil recovery (as defined below), and not just to xanthan gum solutions.

According to the present invention, we provide a process for preparing a solution of a polymer for use in "polymer-based" oil recovery. By "polymer-based oil-recovery", we mean a process such as described above which involves injection of a simple polymer solution and which does not involve the use of surfactants with the polymer. It therefore inherently follows that the present process is one in which surfactant is not added to the polymer solution.

According to the present invention, there is provided a process for preparing a polymer solution for use in "polymer based" oil recovery, which comprises adding to water the polymer in the form of an aqueous solution, a dry particulate solid or a suspension in a non-aqueous liquid, and also adding a complexing agent for multivalent ions and, where the solution so formed does not already contain an alkali metal salt, subsequently incorporating therein an alkali metal salt.

Preferably the solution prepared by the present process is obtained from a preconcentrate of the polymer and the complexing agent which can then be diluted or dissolved on site to give the injection solution. As is conventional when making up polymer solutions for use in oil recovery, the solution may be based on an alkali metal salt solution such as a solution of sodium chloride or sodium sulphate. When a salt solution is used, and for some reason which we are unable to explain, we find that better injectability is obtained by first combining the polymer and complexing agent than when adding the complexing agent to a prepared dilute solution of the polymer in the salt solution. We also find that solutions prepared using the present process have better optical clarity than those prepared without the inclusion of complexing agent.

Where the polymer is a microbial polysaccharide, an aqueous solution thereof is conveniently formed by cultivating a polysaccharide-producing strain of a microorganism in a nutrient medium and subjecting the broth so formed to treatment by a process to remove residual solids e.g. of size greater than 3 microns. Typical processes include filtration, centrifugation and enzyme treatment and are well known in the microbial polysaccharide field.

Alternatively, any solid polymer can be added to water to form the solution. The solid may be a dry powder or granulated material or, as in the case of xanthan, may be formulated as a suspension in a non-aqueous liquid such as alcohol or liquid paraffin. This dry powder or suspension may conveniently also contain the complexing agent.

A combination of the polymer and the complexing agent, either as a dry powder or granulated material or as a suspension in a non-aqueous liquid constitutes a further feature of this invention. In the case of a microbial polysaccharide gum, such as xanthan, the combination may conveniently be prepared by adding the complexing agent, especially sodium hexametaphosphate, to a polysaccharide-containing broth and co-precipitating the combined polymer and complexing agent.

The addition of the complexing agent may be effected either just before the microbial cells are removed by filtration, centrifugation etc., or afterwards. The co-precipitation may be obtained by addition of a precipitant for the polymer which also precipitates the complexing agent, for example, and alcohol such as isopropanol.

Alternatively, the combination may be prepared by simple mixing of the two isolated ingredients.

It is difficult to rationalise the present invention on the basis of the current theories discussed above regarding aggregation upon injection of xanthan gum into alkaline formations; evidently some complexing effect occurs but it is not clear why benefits should be obtained, for example, with hydroxyethyl cellulose solutions for injection at non-alkaline pH. Equally it is difficult to suggest a reason why the order of mixing should be important.

Especially when the injection solution is to contain a salt such as sodium chloride or sulphate, we find that better results are obtained by forming an initial solution of the polymer and the complexing agent and then adding the salt. If the order is reversed and the salt added before the complexing agent, the injectability is typically intermediate between that of the conventional solution without complexing agent and that of the solution prepared in the preferred order. That the order should be significant is particularly surprising since the action of the complexing agent should be unaffected by the presence of monovalent salts such as sodium chloride or sulphate.

It is, however, readily apparent that the present effect is not the same as obtains for the prior art discussed above since the process now provided involves the use of polymer solutions free from residual solids and to which no surfactant is added.

The process according to the present invention can be contrasted from that described in U.K. Pat. No. 1,546,560 where xanthan gum is rehydrated in fresh water containing no complexing agent, before addition of salt. We find that addition of the complexing agent gives a distinct advantage over the use of fresh water alone, the filtration rate being increased by a third or more.

Examples of the complexing agent which may be used include sodium hexametaphosphate such as is available under the trade mark "Calgon", ethylenediamine tetraacetic acid (EDTA) and salts of EDTA. The amount of complexing agent employed is not critical, though a preferred range for the concentration in the final injection solution is 0.01 to 2.0% by weight.

The polymer incorporated in the solution may be any water-soluble polymer of use in oil recovery. Typical polymers include microbial polysaccharide gums, polyacrylamides and cellulose derivatives. The preferred microbial polysaccharide is xanthan. Other microbial polysaccharides include $\beta$-1,3-glucan gums, e.g. that sold under the trade mark "Polytran" by Ceca, in France, obtained from the fungus *Sclerotium glucanicum*. Acrylamide polymers are well established in oil recovery processes.

As well as microbial polysaccharide gum and acrylamide polymers, the invention can employ other polymers such as hydroxyethyl cellulose and related cellulosic materials. The amount of polymer used will depend on the required viscosity for the injection solution. By way of example, we mention that xanthan gum gives effective results when used at a concentration of about one gram per liter.

In the preferred process, a preconcentrate of the complexing agent and the polymer is formed which can then be diluted. Xanthan gum is usually obtained as a fermentation broth containing 20 to 50, typically 30 g/l of the gum. In view of the effective concentration mentioned above of about 1 g/l in the injection solution, it follows that xanthan gum concentrates can conveniently be formulated as approximately 30x concentrates by incorporating in the broth 30 times the ultimately required concentration of complexing agent after removal from the broth of solids greater than 3 microns. For other polymers, like considerations apply and convenient concentrations for the preconcentrates can readily be worked out.

The present invention is illustrated by the following non-limiting examples (all % values are by weight).

EXAMPLE 1

Xanthan fermentation broth (obtained from fermentation of *Xanthomonas campestris*) was diluted and centrifuged to remove cellular debris. The following solutions were prepared (a) by diluting this solution with sodium chloride solution to give a solution containing 3% sodium chloride and 0.1% polymer (the control), (b) by diluting this solution with a solution of a complexing agent, sodium hexametaphosphate, and then adding solid sodium chloride to give a solution containing 0.25% hexametaphosphate, 3% sodium chloride, and 0.1% polymer, the sodium chloride being added last.

The injectability of the solutions was then assessed by filtering the solutions at 20 psi and at room temperature through an Ap 200 millipore prefilter and a 0.8μ Millipore filter and measuring the rate of filtration. The rate was determined after various volumes had been collected. The results are presented in Table 1.

TABLE 1

| Volume Through Filter (ml) | Filtration Rate ml sec$^{-1}$ | |
|---|---|---|
| | Solution (a) Control | Solution (b) |
| 50 | 1.1 | 2.2 |
| 75 | 1.0 | 2.0 |
| 100 | 0.9 | 1.9 |
| 150 | 0.8 | 1.5 |

The Millipore filter evaluation is based on that described by Lipton (op. cit.), in which a Millipore filter is used as a convenient approximation for a porous rock.

EXAMPLE 2

The following solutions of hydroxyethyl cellulose (HEC) were prepared (a) 0.2% HEC in a 3% sodium chloride solution (control) (b) 0.2% HEC in solution with 0.2% sodium hexametaphosphate plus 3% sodium chloride, the sodium chloride being added last. The filterabilities of these solutions were assessed using the method described in Example 1. The results are presented in Table 2.

TABLE 2

| Volume Through Filter (ml) | Filtration Rate (ml sec$^{-1}$) | |
|---|---|---|
| | Solution (a) Control | Solution (b) |
| 100 | 1 | 1.4 |
| 200 | 0.8 | 1.3 |
| 320 | 0.7 | 1.1 |

EXAMPLE 3

The following solutions of a β-1,3-glucan gum produced by the fungus *Sclerotium glucanicum* and available under the trade mark "Polytran" From Ceca, France were prepared (a) 0.2% Polytran in 3% sodium chloride solution (control), (b) 0.2% Polytran in solution with 0.2% sodium hexametaphosphate plus 3% sodium chloride, the sodium chloride being added last. The filterabilities of these solutions were assessed using the method described in Example 1 and the results are presented in Table 3.

TABLE 3

| Volume Through Filter (ml) | Filtration Rate (ml sec$^{-1}$) | |
|---|---|---|
| | Solution (a) Control | Solution (b) |
| 100 | 1.6 | 1.9 |
| 200 | 1.0 | 1.5 |
| 320 | 0.6 | 1.2 |

EXAMPLE 4

The effect of sodium hexametaphosphate on the optical clarity of polymer solutions was studied. Solutions containing 1% polymer (xanthan or Polytran gum) and either 0% or 1.0% hexametaphosphate were prepared. The optical clarity of the solutions was assessed using a colorimeter, the scale used being arbitrary.

The results are presented in Table 4.

TABLE 4

| Polymer | Colorimeter Reading | |
|---|---|---|
| | 0% hexametaphosphate | 1.0% hexametaphosphate |
| Xanthan* | 0.75 | 0.45 |
| Polytran | 0.65 | 0.20 |

*bacterial cells removed by enzyme treatment.

EXAMPLE 5

Enzyme-clarified xanthan gum was used to prepare the following aqueous solutions:
(a) 0.2% xanthan gum plus 3% sodium chloride (control)
(b) 0.2% xanthan gum plus 0.1 M EDTA (ethylenediamine tetraacetic acid) and 3% sodium chloride, the sodium chloride added last.

The filterabilities of these solutions were assessed using the method described in Example 1, and the results are presented in Table 5.

TABLE 5

| Volume through Filter (ml) | Filtration Rate (ml sec$^{-1}$) | |
|---|---|---|
| | Solution (a) (Control) | Solution (b) |
| 110 | 0.7 | 1.0 |
| 180 | 0.3 | 0.7 |
| 360 | 0.1 | 0.4 |

EXAMPLE 6

The effect of the order of addition of hexametaphosphate and salt to polymer solutions on the filterability of those solutions was studied. The following solutions containing 0.1% xanthan, clarified by centrifugation, were prepared: (a) xanthan gum was dissolved in 3% sodium chloride solution, (b) xanthan gum was dissolved in 3% sodium chloride solution and then sodium hexametaphosphate was added to a final concentration of 0.2%, (c) xanthan gum was dissolved in 0.2% sodium hexametaphosphate solution and then sodium chloride was added to a final concentration of 3%. The filterabilities of these solutions were assessed using the method described in Example 1. The results are presented in Table 6. From the table, one can appreciate the improved filterability (and thus improved injectability) of solutions prepared using the present process; the beneficial effect obtained by adding the complexing agent before the sodium chloride is especially marked.

TABLE 6

| Volume Through Filter (ml) | Filtration Rate ml sec$^{-1}$ | | |
|---|---|---|---|
| | Solution (a) | Solution (b) | Solution (c) |
| 90 | 2.3 | 3.3 | 4.5 |
| 120 | 1.7 | 3.0 | 4.5 |
| 160 | 1.3 | 2.7 | 4.5 |
| 200 | 1.1 | 2.0 | 4.5 |

EXAMPLE 7

The procedure of Example 1 was repeated, but using a commercially available polyacrylamide of the type useful in oil recovery, known as DM1 Hiper-pol. Solutions were made up (a) containing 0.1% polymer and approximately 3% sodium chloride and (b) also containing 0.25% sodium hexametaphosphate (Calgon) added before the salt. The prefilter was Millipore AP 20 042 00.

The results are given in Table 7:

TABLE 7

| Weight through filter (g) | Filtration Rate of Sec$^{-1}$ | |
|---|---|---|
| | Solution (a) Control | Solution (b) |
| 10 | 0.17 | 0.28 |
| 50 | 0.12 | 0.23 |
| 100 | 0.08 | 0.16 |
| 150 | 0.05 | 0.12 |
| 180 | 0.05 | 0.10 |

EXAMPLE 8

A 1% solution of xanthan gum, clarified by centrifugation, was prepared in a conc. (ca. 10%) solution of sodium hexametaphosphate. A similar 1% solution was prepared as a control in fresh water (containing no hexametaphosphate). Both solutions were diluted with hard brine (2% NaCl, 0.2% CaCl$_2$) to give (a) 0.1% polymer in hard brine; (b) 0.1% polymer+1% NaHMP in hard brine.
The filterabilities of these solutions were assessed as in Example 1 and the results are shown in Table 8.

TABLE 8

| Volume through filter (ml) | Filtration Rate ml sec$^{-1}$ | |
|---|---|---|
| | Solution (a) Control | Solution (b) |
| 50 | 0.71 | 0.94 |
| 100 | 0.46 | 0.64 |
| 150 | 0.34 | 0.48 |
| 180 | 0.29 | 0.39 |

EXAMPLE 9

The procedure of Example 8 was repeated, but sea water (collected off the South Coast of England and filtered through a 5μ Millipore filter) was used instead of hard brine. The results are shown in Table 9.

TABLE 9

| Volume through filter (ml) | Filtration Rate ml sec$^{-1}$ | |
|---|---|---|
| | Solution (a) (Control) | Solution (b) |
| 50 | 0.5 | 0.61 |
| 100 | 0.3 | 0.39 |
| 150 | 0.21 | 0.29 |
| 180 | 0.16 | 0.24 |

EXAMPLE 10

To a xanthan fermentation broth (ca 2.5% xanthan) was added to conc. solution of sodium hexametaphosphate to give a 1:1 wt. ratio of polymer to complexing agent. A control solution was prepared by diluting the broth with an equal volume of fresh water. Both solutions were centrifuged to remove cells, and then isopropanol was added to effect co-precipitation of xanthan gum and the complexing agent. The product was dried and milled. The following solutions were prepared:
(a) Control: 0.01% polymer in 3% NaCl
(b) 0.2% NaHMP/polymer co-precipitate in 3% NaCl (i.e. approximately 0.1% polymer). The filter abilities were measured as in Example 1 and the results are given in Table 10.

TABLE 10

| Volume through Filter (ml) | Filtration Rate (ml sec$^{-1}$) | |
|---|---|---|
| | Solution (a) (Control) | Solution (b) |
| 50 | 0.37 | 1.7 |
| 150 | 0.13 | 0.78 |

We claim:

1. A process for preparing a polymer solution for use in "polymer based" oil recovery, which comprises, in the absence of surfactant, combining water, a polymer selected from the group consisting of polyacrylamide and cellulose derivative and a complexing agent for multivalent ions and, where the solution so formed does not already contain an alkali metal salt, incorporating therein an alkali metal salt.

2. A process according to claim 1, in which the polymer is selected from the group consisting of a substantially cell-free microbial polysaccharide gum, polyacrylamide and a cellulose derivative.

3. A process according to claim 2, in which the polymer is selected from the group consisting of xanthan gum, a β-1,3-glucan gum, and hydroxyethylcellulose.

4. A process according to claim 2, in which the polymer is a microbial polysaccharide in the form of an aqueous solution formed by cultivating a polysaccharide-producing strain of a microorganism in a nutrient medium and subjecting the broth so formed to treatment by a process to remove residual solids.

5. A process according to claim 2, in which the polymer is a microbial polysaccharide in the form of a particulate solid or a suspension also containing the complexing agent.

6. A process according to claim 4 or claim 5, in which the microbial polysaccharide is xanthan gum.

7. A process according to claim 1, in which the complexing agent is added to an aqueous solution of polymer before dilution with water, in an amount to provide the required concentration in the diluted solution for oil recovery.

8. A process according to claim 7, in which the complexing agent is added in an amount to provide a concentration of 0.01 to 2.0% by weight in the diluted solution.

9. A process according to claim 1 in which the complexing agent is sodium hexametaphosphate, ethylenediamine tetraacetic acid, or a salt of ethylenediamine tetraacetic acid.

10. A process according to claim 1, in which the alkali metal salt is sodium chloride or sodium sulphate.

11. A process for preparing a polymer solution for use in "polymer based" oil recovery, which comprises in absence of surfactant, combining, the polymer and a complexing agent for multivalent ions and then diluting the solution so formed with mixture of an alkali metal salt.

12. A surfactant-free suspension of xanthan gum in a non-aqueous liquid together with a complexing agent for multivalent ions.

13. A surfactant-free particulate solid comprising a combination of a polymer for use in oil recovery with a complexing agent for mutivalent ions.

14. A solid according to claim 12, in which the polymer is microbial polysaccharide, the solid combination having been co-precipitated from solution in a culture broth.

15. A solid according to claim 14, in which the polysaccharide is xanthan.

16. A process according to claim 1, in which the water, polymer and complexing agent are combined in the absence of the alkali metal salt and said alkali metal salt is subsequently incorporated into the solution so formed.

17. A process according to claim 1, or 11 in which said polymer and complexing agent are combined in dry form and the resulting dry combination is combined with an aqueous solution of said alkali metal salt.

18. A process according to claim 1 in which the polymer is hydroxyethyl cellulose.

* * * * *